United States Patent [19]

Chavarria et al.

[11] Patent Number: 4,979,519

[45] Date of Patent: Dec. 25, 1990

[54] HEAD POSITIONING SYSTEM FOR ACCURATE CRANIAL ALIGNMENT AND DIMENSION IN MAGNETIC RESONANCE

[75] Inventors: Lazaro Chavarria, Missouri City; Tommie J. Morgan, Houston, both of Tex.

[73] Assignee: Board of Regents, University of Texas System, Austin, Tex.

[21] Appl. No.: 190,459

[22] Filed: May 5, 1988

[51] Int. Cl.$^5$ .................... A61F 11/00; A61B 5/03; A61G 13/00; A61C 9/00
[52] U.S. Cl. .................................. 128/857; 128/777; 269/328; 433/44
[58] Field of Search .............. 128/870, 871, 869, 849, 128/89 A, 861, 857; 433/44, 45, 46, 47, 68, 69, 72, 73; 269/328

[56] References Cited

U.S. PATENT DOCUMENTS

| | | | |
|---|---|---|---|
| 1,674,088 | 6/1928 | Bodine | 433/73 |
| 1,944,601 | 1/1934 | Gulick | 433/72 |
| 2,202,748 | 5/1940 | Solo | 128/89 A |
| 2,220,734 | 11/1940 | Shanahan | 433/69 |
| 2,299,285 | 10/1942 | Taylor, Jr. | 433/44 |
| 2,418,648 | 4/1947 | Kile | 433/69 |
| 2,554,277 | 5/1951 | Taylor, Jr. | 433/69 |
| 2,814,876 | 12/1957 | Stuart | 433/69 |
| 2,829,435 | 4/1958 | Kazis | 433/69 |
| 2,841,871 | 7/1958 | Miller | 433/68 |
| 2,863,216 | 12/1958 | Lichtman | 433/69 |
| 3,058,217 | 10/1962 | Joffee | 433/69 |
| 3,060,935 | 10/1962 | Riddell | 128/861 |
| 3,069,774 | 12/1962 | Levey | 433/73 |
| 3,074,166 | 1/1963 | Skallerup | 433/69 |
| 3,131,475 | 5/1964 | Craigo | 433/72 |
| 3,577,639 | 5/1971 | Lee | 433/69 |
| 3,724,099 | 4/1973 | Stuart | 433/68 |
| 4,182,322 | 1/1980 | Miller | 128/869 |
| 4,197,855 | 4/1980 | Lewin | 128/653 |
| 4,256,112 | 3/1981 | Kopf | 269/328 |
| 4,292,026 | 9/1981 | Yokota | 433/69 |
| 4,303,077 | 12/1981 | Lewin et al. | 128/777 |
| 4,400,820 | 8/1983 | O'Dell | 128/869 |
| 4,550,713 | 11/1985 | Hyman | 128/849 |
| 4,595,022 | 6/1986 | Schorr | 128/777 |
| 4,639,220 | 1/1987 | Nara | 433/68 |

Primary Examiner—Robert A. Hafer
Assistant Examiner—Michael Brown
Attorney, Agent, or Firm—Arnold, White & Durkee

[57] ABSTRACT

The present invention relates to a portable head positioning system for the establishment and measurement of a variety of different head orientations for the purposes of magnetic resonance imaging. The present system include a head engagement assembly and a mouthpiece or orientation component which cooperate to enable reproducible imaging.

35 Claims, 5 Drawing Sheets

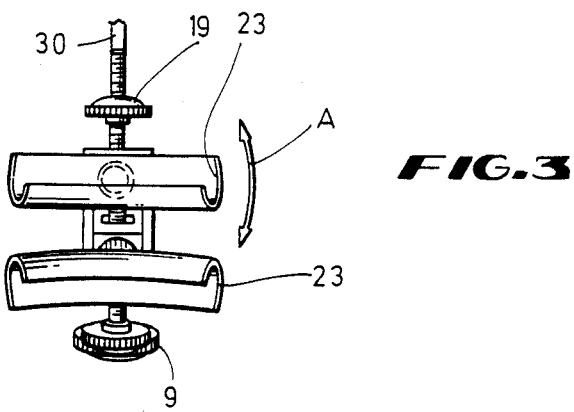
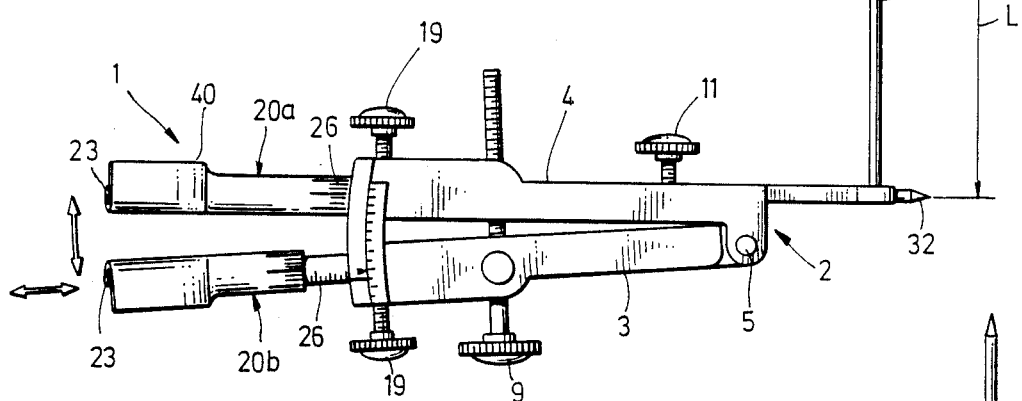
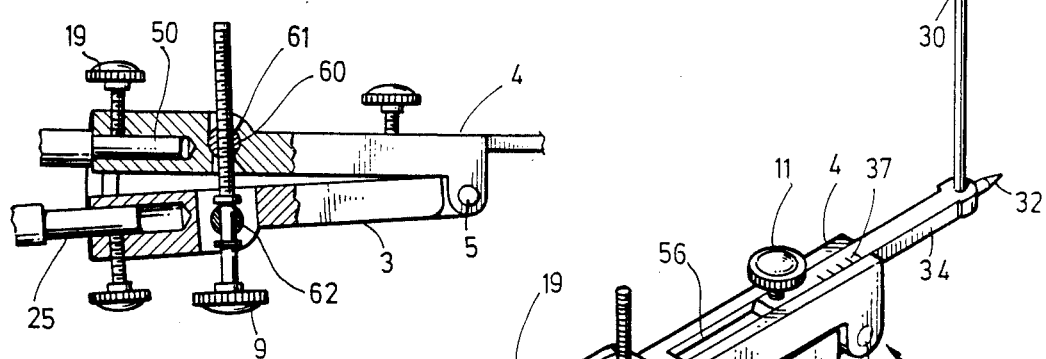
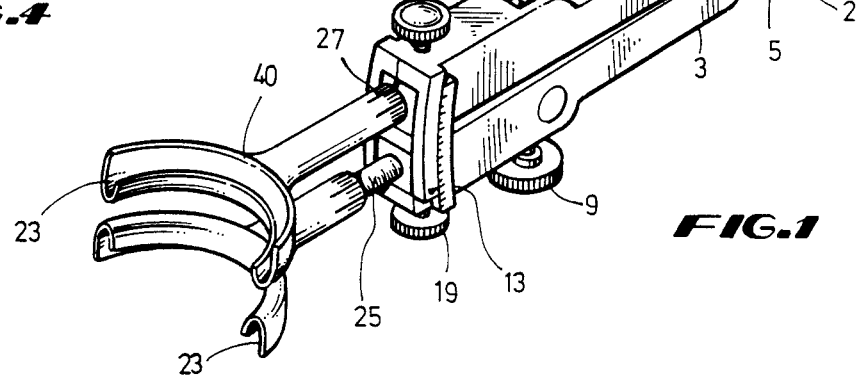

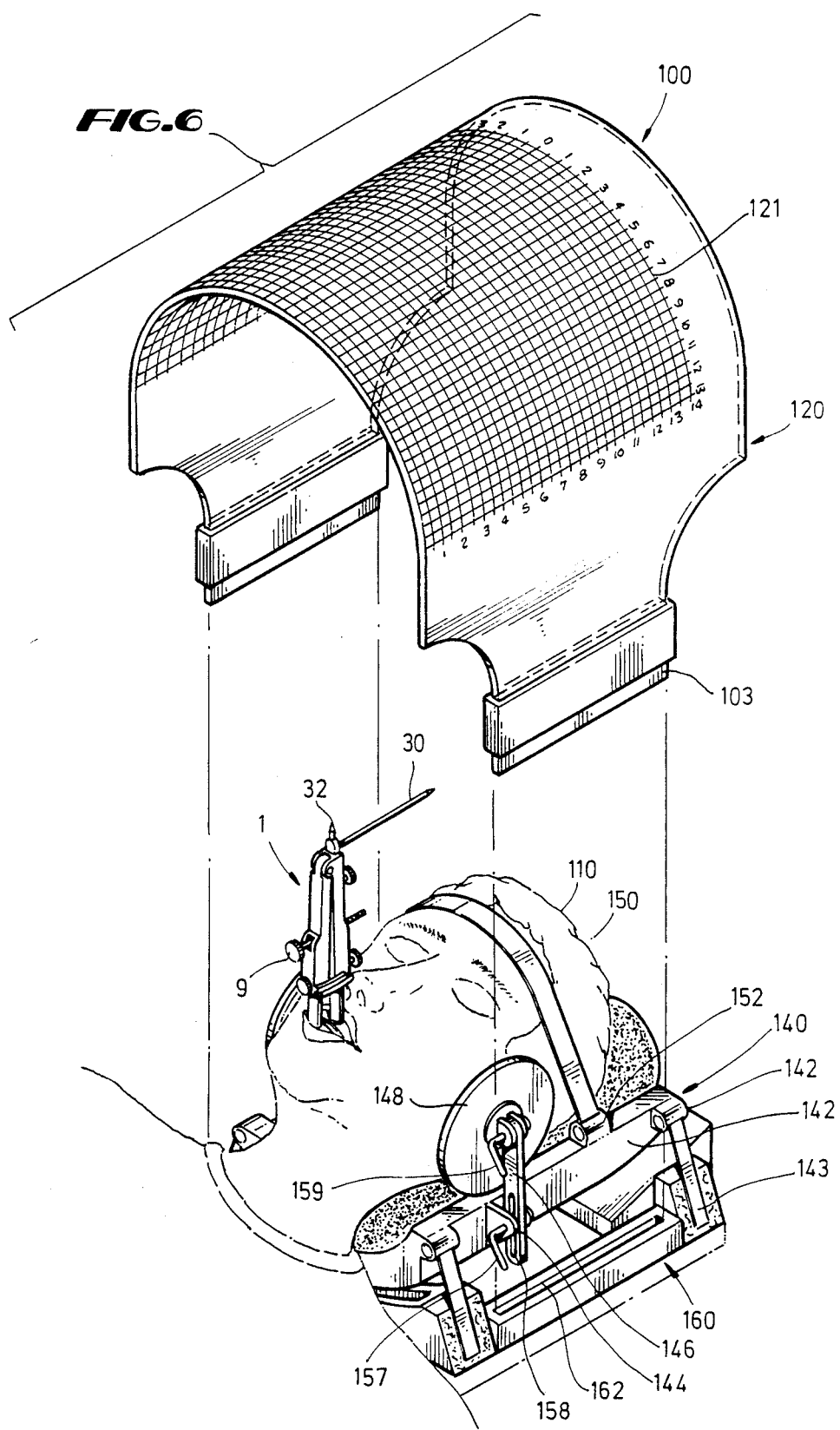

HEAD POSITIONING SYSTEM FOR ACCURATE CRANIAL ALIGNMENT AND DIMENSION IN MAGNETIC RESONANCE

BACKGROUND OF THE INVENTION

1. Field of the Invention:

The present invention generally relates to a head positioning system to aid in the accurate, planar visualization of temporomandibular joint structures. More particularly, the present invention relates to a head positioning and alignment device which provides a fixed, reproducible geometry of a patient's head with reference points from which precise positioning of the TMJ structure may be made possible. The present device also provides for accurate head positioning to facilitate cephalometric measurement using MR imaging.

2. Description of the Prior Art:

Internal derangement of the temporomandibular joint (TMJ) is an abnormal relationship between the mandibular condyle and the disc (meniscus). TMJ disease has been reported in random surveys to range in prevalence from 28 percent to 37 percent of the general population. It is myofacial pain dysfunction (MPD). This dysfunction, if left untreated, may progress to degenerative joint disease (osteoarthritis) involving the condyle, disc and glenoid fossa.

Patients afflicted with osteoarthritis usually complain of joint pain principally in the region of the posterior of the condylar, head, neck and tragus of the ear. These areas coincide with the anatomical position of the bilaminar zone of the TMJ. Surgical management of osteoarthritis usually consists of a meniscoplasty or meniscectomy with or without osseous recontouring.

The patient's medical history as well as clinical and diagnostic imaging examinations are extremely important in the establishment of a definitive diagnosis of any dysfunction. This history may include an episode of trauma, which can be a result of either a direct jaw injury or a "whiplash" type of injury. However, in many cases there is no history of trauma and the first sign of an internal derangement is a painless "click" in the joint during opening. Ultimately this condition progresses to crepitation in the joint which could be indicative of a disc perforation and/or degenerative joint disease.

Radiodiagnosis is an essential tool in determining the morphology and structural changes occurring in the temporomandibular articulation. As compared to other articular joints, the articulation is exceptional because of its unique anatomic configuration and complicated function. TMJ anatomy is complex and includes tortuous bony surfaces and intricate soft tissue configurations.

The multiple densities of the articulation and the variable shape of its components have emphasized the need for standardized radiographic techniques that will provide accurate and repeatable images of the structures of interest on a gross recording medium. The preferred radiographic technique, therefore, must provide images of articulation in different planes, as well as providing images produced at different sessions for comparison and evaluation. The contemporary technique to accomplish these goals is tomography.

A variety of methods have been proposed to describe the positioning of the patient's head for tomographic examination of temporomandibular articulation. Both Shore, *Oral Surg, Oral Med, Oral Pathol*, Vol. 13, pp. 341-350 (1960) and Baker, *Radiol. Clin. North Am.*, vol. 14, pp. 105-127 (1976) have proposed that the average condyle angulation should be established at 20° in the horizontal plane. Other investigators as well have suggested an individualized technique of head positioning for the articulation examination in which the angulation of the horizontal condyle axis may be determined from the submental vertex radiograph of the subject's head.

In order to develop a technique of corrected lateral cephalometric and corrected antero-posterior cephalometric tomography of the articulation, however, a cephalometric device is needed to allow the patient's head to be positioned according to the previously determined horizontal and vertical angles of each condyle. Preferably, this device should have at least two measurable degrees of freedom. Further, such a device should be capable of measuring and reproducing a desired jaw position in a given patent.

SUMMARY OF THE INVENTION

The present invention relates to a portable head positioning and alignment system for application in accurate planar visualization of temporomandibular joint structures. The present invention has particular application in visualization techniques utilizing MR imaging.

The present system generally comprises a multiple geometry head engagement assembly adapted to be secured inside the head coil of a conventional CT scanning device. This head assembly is configured such that the patient's head may be positioned in a fixed, set, and reproducible position. The system further includes a mouthpiece or similar orientation component which cooperates with the head engagement assembly to calibrate the position of the head via fixed reference points.

Preferably, an arcally calibrated face plate is positioned above and in a fixed position relative to the head engagement assembly, such that the position of objects between the face plate and the head engagement assembly may be calibrated or determined. This face plate is preferably a transparent member bearing a system of coordinates through which the coordinates of a particular such object may be observed. The face plate, in effect, serves as a chart or grid for locating or positioning the object.

The head engagement assembly is preferably comprised of a headrest component movably disposed within a headpiece component via a roller and track assembly. This roller and track assembly is preferably provided with a means to lock the headrest in any desired position relative to the headpiece, said relative position being measurable via a location indicating system. Preferably, means are also provided to immobilize the patient's head securely within the assembly.

The mouthpiece component is configured such that it may be customized to the position and orientation of the teeth or craniofacial position of a given patient. This component generally includes a bitepiece secured to an expandable, scissor-like body element, the body element defining a spatial indicator at its distal end. The mouthpiece element is designed such that the mouth opening of a given patient may be quantified and hence precisely reproduced.

In some embodiments, this mouthpiece may be provided with an aspiration or suction apparatus to facilitate the removal of undesired saliva generated during a given procedure.

The use of the mouthpiece component in conjunction with the head engagement assembly allows precise calculation of the orientation of the patient's head at any time, thereby allowing reproducible positioning for an MR imaging examination or other medical procedure where precise quantitative reproducible positioning is required. Thus, diagnostic analyses and comparison may be made over an interrupted time interval by accurately reproducing the desired orientation of the TMJ or other craniofacial structure.

The present invention presents many advantages over the art. One such advantage is the ability of the invention to provide a fixed, reproducible geometry of a patient's head utilizing set reference points from which precise positioning of the TMJ structure may be possible.

Another advantage of the present invention is its ready compatibility with all types of existing MR imaging systems.

BRIEF DESCRIPTION OF THE DRAWINGS

FIG. 1 illustrates a perspective view of the mouthpiece.

FIG. 2 illustrates a side view of the mouthpiece illustrated in FIG. 1.

FIG. 3 illustrates an end view of the mouthpiece illustrated in FIG. 1.

FIG. 4 illustrates a side section of the mouthpiece illustrated in FIG. 1.

FIG. 6 illustrates a perspective view of the head positioning system with the foreplate shown raised above its normal operating positioning.

DETAILED DESCRIPTION OF PREFERRED EMBODIMENT

Figure 5:
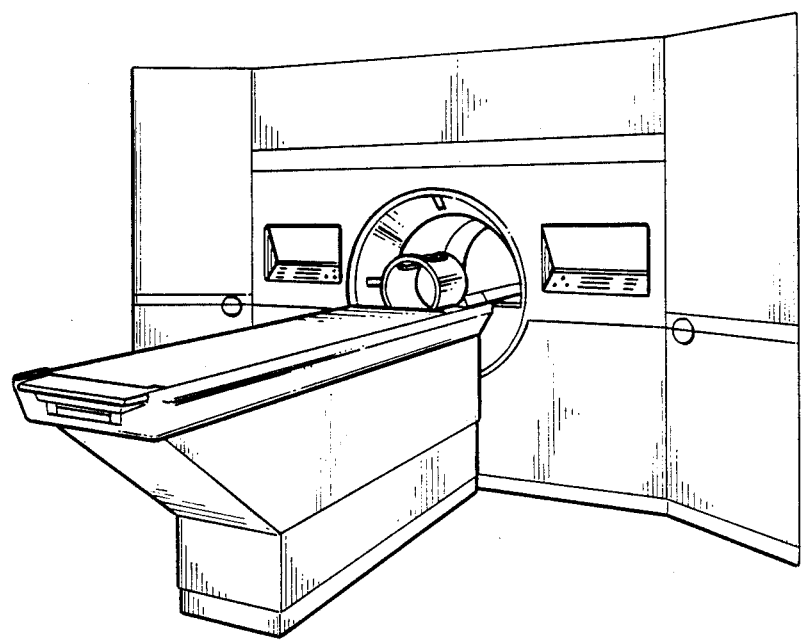
FIG. 5 illustrates a perspective view of a magnetic resonance (MR) imaging system.

The present invention is generally comprised of a mouthpiece and a separate head engagement assembly. These two components cooperate to enable the physician or technician to establish a fixed, reproducible geometry of a patient's head where such is required for the medical procedure from which cephalometric measurements may be made. Such medical procedures include diagnostic imaging of the TMJ, nasopharynx, orbits, oral cavity, inner ear, or other complex anatomies of the head or neck.

The mouthpiece component is designed to be inserted in the mouth of a patient and then adjusted to establish the desired viewing angles of the TMJ or other structure of interest. A perspective view of a general embodiment of the mouthpiece 1 is seen in FIG. 1. In this figure may be seen the frame 2 comprised of a body member 4 and a hinge member 3 connected about a pivot 5. The relative position of the body 4 and hinge 3 members may be adjusted via an adjustment screw 9. Screw 9 is threadedly disposed between the body 4 and the hinge 3 as shown, such that any desired facial structure position may be established, quantified and fixed. The angle of this orientation may be measured via a scale 13.

Referring to both FIG. 1 and FIG. 2, both the body 4 and hinge member 3 are coupled at their proximal ends to bitepiece elements 20a and 20b. In a preferred embodiment, bitepiece elements 20a and 20b are configured to receive impression material or other malleable material (not shown) at their outer, teeth engaging surfaces 40. In such embodiments, therefore, the bitepieces may be provided with a recessed groove or indentation 23 so as to facilitate the retention of this impression material.

Referring to FIGS. 1—4, both the body 4 and hinge 3 are provided with a cylindrical bore 50 to accommodate bitepieces 20 via slide shafts 25. These shafts 25 may be locked into the frame 2 via lock screws 19. In such a fashion, bitepieces 20 may be independently moved axially relative to the frame 2 in order to accommodate any relative juxtaposition of the upper and lower jaws in the form of overbite, underbite, etc. Alternatively, this setup enables bitepieces 20 to be removed entirely from the frame 2 for cleaning or storage. Shafts 25 may also be rotated relative to the frame 2 as shown by arrow A in FIG. 3. In preferred embodiments, shafts 25 are provided with graduations 26 to allow measurement of both the rotation and axial movement of bitepieces 20, and hence facilitate recordation and duplication of a given jaw orientation.

Bitepieces 20 and support shafts 25 may be integrated as one unit or formed separately in order to best facilitate customization and storage. In such a fashion, the bitepiece component 20 in conjunction with an appropriate impression material may be customized for a given patient and then removed for subsequent reinsertion and/or comparison. Alternatively, the bitepiece 20 may be coated with a nonadhering material, e.g., Teflon, such that the impression material may be inserted and then easily removed from the bitepiece 20 for subsequent reinsertion.

The mouthpiece 1 is adapted to be used in conjunction with the head engagement assembly 100 to calibrate the exact orientation of the head via fixed reference points. This is achieved via an indicator 30 situated at the distal end of the frame 2. This indicator 30 is preferably fixed within the frame 2 and established at a set known length "L". Alternatively, the indicator 30 may be slidably attached to the frame 2 and graduated such that a given dimension may be reproduced in a plane parallel to the patient's head.

Referring to FIGS. 1 and 2, the relative axial position of the indicator 30 along the frame 2 is also variable. In a preferred embodiment, a bracket 34 is slidably fitted within a groove 36 defined within the body member 4 such that the bracket 34 and indicator 30 may be adjusted relative to the patient's head. This axial position along the axis of body member 4 may be fixed via an adjustment screw 11, and read via a scale 37 formed on the bracket 34. In a preferred embodiment, the frame is also provided with a tapered surface or "sight" 32 situated at the distal of the frame 2. The sight 32 is generally perpendicular to the indicator 30 and parallel to the axis of body member 4. The nature and function of sight 32, in conjunction with indicator 30, will be further discussed herein.

In cases where the patient is younger or particularly prone to gagging, the use of a mouthpiece such as that above described may be objectionable. This may particularly be true when a given examination takes place over an extended period. In such cases, therefore, it may be desirable to incorporate within the mouthpiece a quick release mechanism. Such a quick release mechanism is illustrated in FIG. 4. In this illustration, both the body 4 and hinge member 3 are internally configured to accept a retaining fastener 60, said fastener 60 held in place by a lip 61 formed in the frame 2. These fasteners 60 are preferably spherical in shape and are provided with a threaded bore 62 to accommodate adjustment screw 9. Fasteners 60 may be formed of nylon or other suitable material to frictionally restrict their movement within the cavity formed by lip 61, yet resilient enough to allow the fasteners 60 to move past lip 61 when considerable pressure is applied to mouthpiece 20 in a direction parallel to the major axis of screw 9. In such a fashion, the patient, by sharply biting down on bitepiece elements 20A and 20B, forces fasteners 60 past lip 61 so that bitepiece elements 20 are drawn together, thus facilitating removal of the mouthpiece assembly 1.

Figure 12:
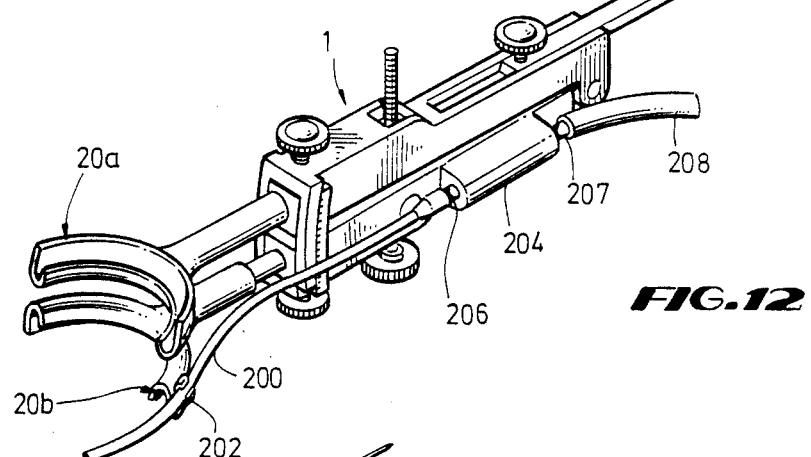
FIG. 12 illustrates a perspective view of an alternate embodiment of the mouthpiece.

During a lengthy examination, excess saliva may accumulate in the patient's mouth. If the mouthpiece element is positioned such as to maintain the mouth in an open position, the patient will be unable to swallow and thus may be prone to gag on such secretions. To address this problem, the mouthpiece element 1 may be provided with an aspiration or suction tube. FIG. 12 illustrates the use of such an aspiration or suction tube 200 in conjunction with the mouthpiece 1. In this embodiment, the mouthpiece 1 is filled with a connector attachment 204, said attachment provided with a male connector 206 adapted to fit snugly into a standard aspiration tube 200 as shown. Preferably, this aspiration tube 200 is passed into the patient's mouth while in close proximity to the bitepiece 20 via an attachment clip 202 molded on the lower bitepiece 20b. To complete this system, a vacuum tube 208 is linked to the other end of the connector 204 via male attachment 207, said tube 208 linked to a conventional vacuum system. In yet other embodiments, the vacuum drawn through the aspiration or vacuum system may be regulated by the patient via a thumbdial or other valving means (not shown). This valving means may be positioned in the vacuum line 208 or situated in the connector itself.

As earlier noted, the mouthpiece element 1 cooperates with the head engagement assembly to accurately establish the position of the patient's head from a series of fixed reference points. The head engagement assembly 100 is seen by reference to FIGS. 6-10, which generally illustrate the component parts of the assembly 100, including the faceplate 120, the headrest 140 and the headpiece 160

Figure 7:
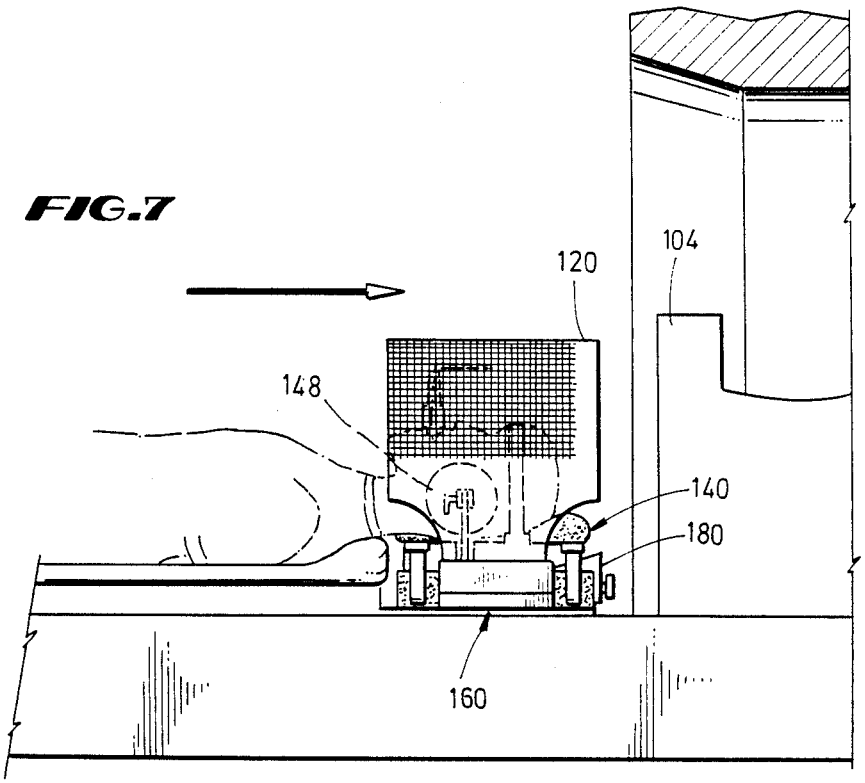
FIG. 7 illustrates a side view of the head positioning system as it may be used in conjunction with the MR system illustrated in FIG. 5.

Referring to FIGS. 6 and 7, the faceplate 120 is configured so as to fit over and around the patient's head 110 at a sufficient distance as to allow ready measurement and adjustment of the mouthpiece 1. So that the orientation of the mouthpiece 1, specifically the relative positions of the indicator 30 and sight 32, may be measured, and hence duplicated in subsequent examinations, the faceplate 120 is preferably provided with a transparent grid 121. This grid is marked so as to allow measurement of the indicator 30 and accompanying sight 32, in both the x and y direction while the mouthpiece is oriented in the patient's mouth.

The faceplate 120 is configured to securely attach to either the headpiece 160 or the headrest 140. In one embodiment, the faceplate 120 may be provided with attachment flanges 103 adapted to fit into corresponding slots 162 provided in the headpiece 160. In such a fashion, the faceplate may be readily removed for any necessary adjustment to the mouthpiece 1. In alternate embodiments, the faceplate 120 may be joined at one edge to the headpiece via a hinge or the like. Other embodiments are also envisioned such as where the faceplate may be slidably attached to the headpiece 160.

Figure 8:
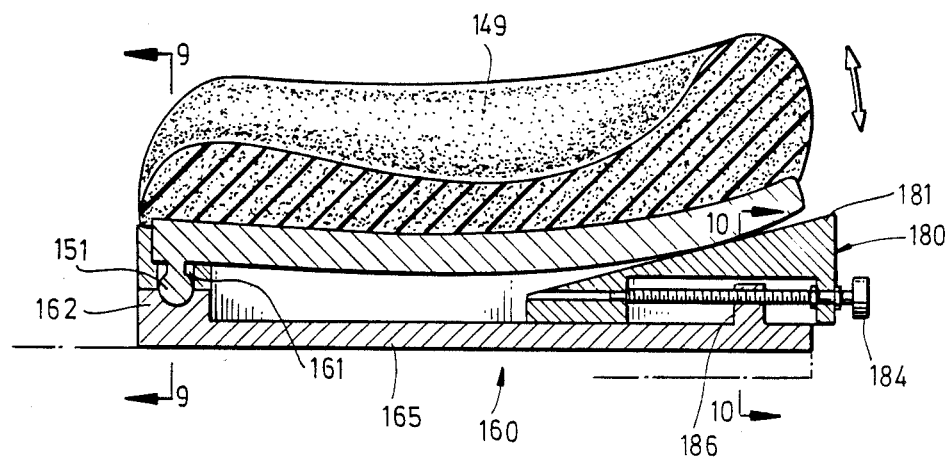
FIG. 8 illustrates a side section of one embodiment of the head engagement assembly.
Figure 9:
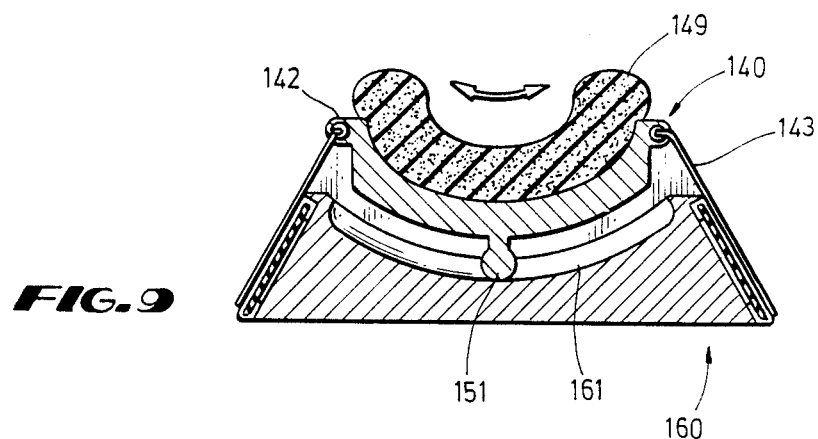
FIG. 9 illustrates an end section of one embodiment of the head engagement assembly as taken through plane 9—9 in FIG. 8.

The headrest component 140 generally comprises a main frame 141 which is configured to support a patient's head 110. In preferred embodiments, the headrest 140 is arcuate or semicircular in end cross section as illustrated in FIG. 9. Similarly, the distal end of the headrest 10 may be upwardly curved as illustrated in FIG. 8 to provide proper support to the head. In preferred embodiments, the headrest 140 is lined with a resilient material 149, such as closed cell foam rubber, to enhance the overall comfort and fit of the apparatus.

Referring to FIGS. 6 and 9, the frame 141 is preferably provided with attachment brackets 152 to accommodate Velcro fasteners 150. In such a fashion, the head 110 may be secured to the headrest 140 in any desired orientation. Similarly, the frame 141 can also be provided with brackets 142 to secure the headrest 140 to the headpiece 160 via fasteners 143.

Figure 11:
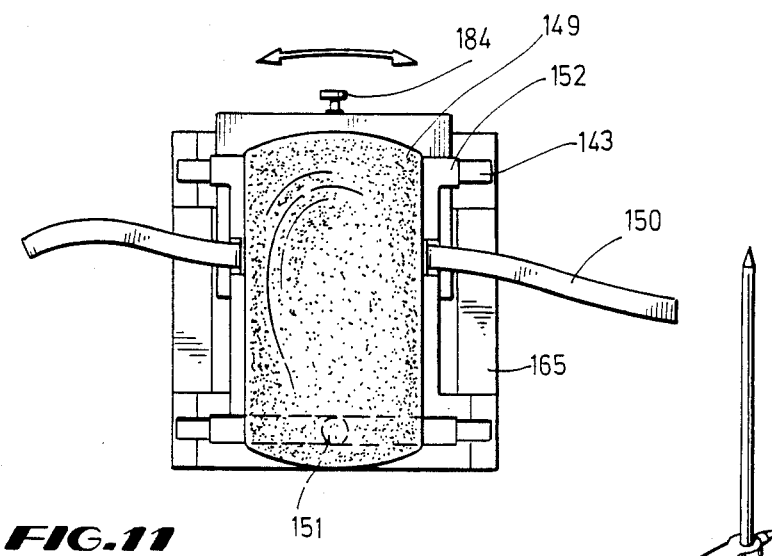
FIG. 11 illustrates a top view of one embodiment of the head engagement assembly as illustrated in FIG. 8.

As noted above and shown in FIG. 9, the headrest 140 is preferably semicircular or arcuate in end cross-section, said shape desirable both for purposes of accommodating the shape of the head and to allow arcuate movement of the headrest 140 relative to the headpiece 160. Referring to FIGS. 8 and 9, headrest 140 is provided at its proximal end with a roller or flange 151 adapted to moveably fit within a groove or slot 161 formed in the headpiece 160. The headrest 140 may thus accommodate a patient's head 110 as it is pivoted several degrees in each direction as illustrated in FIG. 11. When a desired rotation of the head 110 is achieved, the headrest may be secured via fasteners 143 as earlier described.

In a preferred embodiment, the headrest 140 is provided with means to secure one or two pairs of surface coils or specialty coils proximate to the area or areas of investigation. Referring to FIGS. 6 and 7, the surface coils 148 are held at a desired position relative to the patient's head 110 via a flange or bracket 146 coupled to the frame 141 via a retention bracket 144. A variety of differently sized surface coils 148 may be desired dependent on the area of interest or investigation. These surface coils 148 are therefore detachable from the flange 146 via quick release pins 159. Flanges or brackets 146 are coupled to brackets 144 via quick release pins 157, said pins engaging a slot 158 as shown. In such a fashion, maximum versatility in the positioning of the surface coils 148 may be achieved.

The use of the mouthpiece in combination with the head engagement assembly is desired when an analysis of the TMJ structure is undertaken. However, when a cephalometric analysis is conducted, it is often desirable to view the facial structure when the mouth is completely closed. In such a case, therefore, the use of a mouthpiece as previously described will not be possible. Even during such cephalometric analysis, however, an accurate spatial quantification of the patient's head is still necessary.

Figure 13:
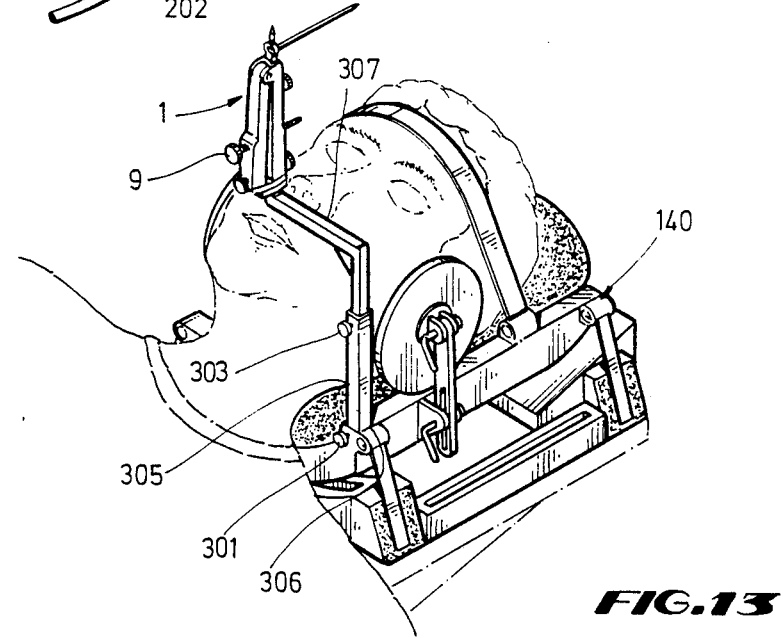
FIG. 13 illustrates an alternate embodiment of the head positioning system.

An alternate embodiment of the present invention is directed toward the occasions when cephalometric analysis is desired. FIG. 13 illustrates an embodiment where the head engagement assembly is provided with an attachment bracket 306, said bracket preferably disposed on the headrest 140 in a plane roughly parallel with the mouth of the patient. A telescoping bracket arrangement 305 and 307 is coupled to the head engagement assembly at 300, the geometry of brackets variable via adjustment screws 301 and 303.

In a preferred embodiment, brackets 305 and 307 are adapted to receive the mouthpiece element via one or two protrusions (not shown) which are adapted to fit into the mouthpiece 1 via bores 50 (See FIG. 4) vacated by the removal of bitepiece elements 20. In such a fashion, the mouthpiece 1 may be secured to brackets 305 and 307 via adjustment screws 9.

Figure 10:
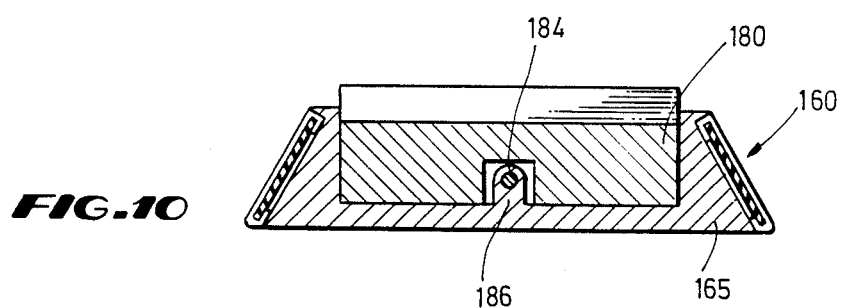
FIG. 10 illustrates an end section of one embodiment of the headpiece as taken through plane 10—10 in FIG. 8.

The headpiece forms the base for the head alignment system and is adapted to be compatible with conventional MR imaging systems. Referring to FIGS. 7, 8 and 10, the headpiece 160 generally comprises a frame 165, said frame including a receiving bracket 162 at its proximal end and an elevation assembly 180 at its distal end. As earlier described, the receiving bracket 162 is provided with a groove or slot 161 to accommodate the rotational flange or roller 151 of the headrest 140. In preferred embodiments, frame 165 is provided with a scale (not shown) to enable measurement of the degree of tilt achieved by the headrest 140 along the slot 161 relative to the headpiece 160.

The elevation assembly 180 generally includes a moveable wedge 181 slidably interposed between the frame 165 and the bottommost portion of the headrest 140. Structurally, the movement wedge 181 is secured to the frame 165 via an adjustment screw 184, said screw threadedly coupled to a mounting bracket 186. Rotation of screw 184 results in longitudinal movement of wedge 180, thus resulting in a vertical movement of the headrest 140. In such a fashion, the patient's head 110 may be vertically oriented or "tilted" to achieve any desired viewing angle of the TMJ. In preferred embodiments, this vertical orientation may be measured via a scale 189 provided on the elevation assembly 180.

As noted, the components of the invention are adapted to be used with conventional MR imaging systems such as those manufactured by Philips, Fisher, General Electric, Somers, etc. as illustrated in FIGS. 5 and 7. Since magnetic resonance imagery applications are thus envisioned, the components of the invention are preferably formed of radiography transparent material such as plastics, nylons, etc.

What is claimed is:

1. A head positioning system, comprising:
   a mouthpiece comprising a frame member, a bitepiece system at one end of the frame member, and a spatial indicator at the other end of the frame member operable to reflect the spatial orientation of the patient's head; and
   a head engagement assembly, said assembly comprising a headpiece, a headrest movably coupled to the head piece, a gridded faceplate adapted to be attached to the headpiece in order to substantially cover the patient's face and measurement means attached to the head piece operable in combination with the spatial indicator for measuring a given head position where, said head engagement assembly is remote from said bitepiece.

2. The head positioning system of claim 1 wherein the mouthpiece frame member is comprised of a first body member and a hinged second member pivotally attached to the first body member to move in a scissor-like fashion.

3. The head positioning system of claim 2 further comprising an adjustment screw operable to provide the scissor-like movement.

4. The head positioning system of claim 2 wherein the bitepiece is comprised of an upper and lower member, the upper member coupled to the first member of the frame and the lower member coupled to the second member.

5. The head positioning system of claim 2 further comprising means to measure the relative position of the first and the second members.

6. The head positioning system of claim 1 wherein the bitepiece is axially movable relative to the frame 7. The head positioning system of claim 6 further comprising means to measure the axial position of the bitepiece relative to the frame.

8. The head positioning system of claim 1 where the bitepiece is rotatable relative to the frame.

9. The head positioning system of claim 8, further comprising means to measure the rotational position of the bitepiece relative to the frame.

10. The head positioning system of claim 1 wherein the spatial indicator is axially movable relative to the frame.

11. The head positioning system of claim 10 further comprising means to measure the axial position of the spatial indicator relative to the frame.

12. The head positioning system of claim 1 further including an aspiration or vacuum means.

13. The head positioning system of claim 1 wherein the headrest includes means to secure a patient's head in immovable relationship with said headrest, and means to secure the headrest to the headpiece.

14. The head positioning system of claim 1 wherein the headrest is movable relative the headpiece in both the x and y direction.

15. The head positioning system of claim 14 further comprising means to measure the spatial relationship of the headrest relative the headpiece.

16. The head positioning system of claim 1 further including an elevation system disposed between the headrest and the headpiece such that axial movement of said elevation system along said headpiece results in a vertical displacement of said headrest.

17. The head positioning system of claim 1 wherein the measurement means comprises a gridded transparent faceplate adapted to encompass the patient's head.

18. The head positioning system of claim 1 further including means to movably secure surface coils proximate to a patient's head for purposes of MR imaging.

19. A head positioning system for planar visualization of TMJ structures, comprising:
   a mouthpiece comprising a frame, a bitepiece system and a spatial orientation system, said frame movably coupled to said bitepiece system at one end, and slidably coupled to said spatial orientation system at a second end; and
   a head engagement assembly comprising a headpiece and headrest movably coupled to the headpiece; the head engagement assembly and mouthpiece operable in combination to measure and establish a given head position in the x, y and z planes, a gridded faceplate adapted to be attached to the headpiece in order to substantially cover the patient's face; where said head engagement assembly is remote from said bitepiece.

20. The head positioning system of claim 19 further including means to measure the relative positions of the frame, the bitepiece and the spatial orientation system.

21. The head positioning system of claim 19 wherein the spatial orientation system comprises an indicator and a sight.

22. The head positioning system of claim 19 further including a vacuum or aspiration means.

23. The head positioning system of claim 19 wherein the headpiece is comprised of a base and a gridded, transparent faceplate, the combination base and faceplate enabling a visual determination of the spatial position of the mouthpiece in both the x and y planes.

24. The head positioning system of claim 19 further including means to position surface coils proximate a desired area on a patient's head.

25. The head positioning system of claim 19 further comprising means to immobilize a patient's head in a given position relative to said headrest.

26. The head positioning system of claim 19 further comprising means to secure the headrest in a desired position relative to the headpiece.

27. A head positioning system, comprising:
a mouthpiece comprising a frame, a bitepiece, and a spatial indicator, said frame comprising a first member pivotally attached to a second member, the combination attached at one end to the bitepiece, and at a second end to the spatial indicator, the combination frame, bitepiece and spatial indicator movably interconnected and further provided with means to measure such relative movement; and
a head engagement assembly comprising a headrest movably coupled to a headpiece via an elevation assembly, said headrest comprised of a base detachably coupled to a gridded faceplate which is adapted to substantially cover the patient's face the combination headrest and headpiece provided with a means to establish a desired head orientation and measure said orientation.

28. The head positioning system of claim 27 wherein the bitepiece includes a means for retaining a given impression material.

29. The head positioning system of claim 27 wherein the bitepiece is removable from the frame.

30. The head positing system of claim 27 further including a vacuum or aspiration means.

31. The head positioning system of claim 27 where the combination headrest and headpiece is adapted to be attached to conventional MR imaging systems.

32. A head positioning system comprising:
(a) a head engagement assembly including:
(1) a headpiece,
(2) a headrest positioned above and pivotably mounted at one end to the headpiece, and
(3) a movably wedge interposed between the other end of the headrest and the headpiece and operable to raise and lower the headrest; and
(b) a gridded face plate adapted to substantially cover the patient's face is supported above the head engagement assembly in calibrated relation to the head engagement assembly.

33. A head positioning system comprising: a vertically, longitudinally and laterally adjustable head engagement assembly adapted to support a person's head in a fixed position with the person in a supine position;
a mouthpiece adapted to be supported above the head engagement assembly in a vertically adjustable position relative to the head engagement assembly; and
calibration means operable in combination with the mouthpiece to indicate the spatial orientation of the person's head a gridded faceplate adapted to be attached to the head engagement assembly in order to substantially cover the patient's face; said head engagement assembly is remote from said mouthpiece.

34. A head positioning system for a person in a supine position comprising:
a headpiece;
a headrest movably mounted at first end to and above the headpiece pivot in a generally vertical plane and to tilt laterally relative to the headpiece;
elevation means interposed between the second end of the headrest and the headpiece operable to pivot the headrest above said first end;
fastening means attached to the headrest operable to fasten a person's head on the headrest;
a mouthpiece, including upper and lower bitepieces adapted to be fitted in a person's mouth and pivotally joined outside the person's mouth, and a spatial indicator at the pivot joint operable to indicate the spacing between bitepieces;
an a really calibrated, transparent gridded face plate adapted to be supported from the head engaging assembly above a person's head and the mouthpiece, said face plate enabling an observer to view a person's head through the face plate and in relation to the a real calibrations on the face plate where said head positioning system is remote from said mouthpiece.

35. The head positioning system of claim 34 further comprising at least one sight attached to the mouthpiece to facilitate location of a person's head on the headrest relative to calibrations on the face plate.

* * * * *

UNITED STATES PATENT AND TRADEMARK OFFICE
CERTIFICATE OF CORRECTION

PATENT NO. : 4,979,519

DATED : December 25, 1990

INVENTOR(S) : Lazaro Chavarria and Tommie J. Morgan

It is certified that error appears in the above-identified patent and that said Letters Patent is hereby corrected as shown below:

In claim 32, column 2, line 6, "movably" should be --moveable--.

In claim 33, column 2, line 25, insert --where-- after "face;".

In claim 34, column 2, line 41 "a really" should be --areally--.

In claim 34, column 2, line 49, "a real" should be --areal--.

Signed and Sealed this

Eleventh Day of August, 1992

Attest:

DOUGLAS B. COMER

*Attesting Officer*     *Acting Commissioner of Patents and Trademarks*